US012422428B2

(12) United States Patent
Atapattu et al.

(10) Patent No.: US 12,422,428 B2
(45) **Date of Patent: *Sep. 23, 2025**

(54) COMPOSITIONS AND METHODS FOR CELL-BASED ASSAYS

(71) Applicant: BIOMADISON, INC., Del Mar, CA (US)

(72) Inventors: Dhammika Atapattu, Madison, WI (US); Ward C. Tucker, Monona, WI (US)

(73) Assignee: BIOMADISON, INC., Del Mar, CA (US)

( * ) Notice: Subject to any disclaimer, the term of this patent is extended or adjusted under 35 U.S.C. 154(b) by 682 days.

This patent is subject to a terminal disclaimer.

(21) Appl. No.: 17/719,742

(22) Filed: Apr. 13, 2022

(65) Prior Publication Data

US 2022/0260555 A1 Aug. 18, 2022

Related U.S. Application Data

(63) Continuation-in-part of application No. 15/817,065, filed on Nov. 17, 2017, now Pat. No. 11,325,954, which is a continuation-in-part of application No. 15/018,621, filed on Feb. 8, 2016, now Pat. No. 10,100,094, which is a continuation of application No. 13/485,537, filed on May 31, 2012, now Pat. No. 9,274,121.

(60) Provisional application No. 61/492,237, filed on Jun. 1, 2011.

(51) Int. Cl.

| | |
|---|---|
| ***G01N 33/542*** | (2006.01) |
| ***C07K 14/00*** | (2006.01) |
| ***C12N 15/85*** | (2006.01) |
| ***G01N 33/58*** | (2006.01) |

(52) U.S. Cl.

CPC .......... *G01N 33/542* (2013.01); *C07K 14/00* (2013.01); *C12N 15/85* (2013.01); *G01N 33/582* (2013.01); *G01N 2333/33* (2013.01)

(58) Field of Classification Search

CPC ............... G01N 33/542; G01N 33/582; G01N 2333/33; C07K 14/00; C12N 15/85

See application file for complete search history.

(56) References Cited

U.S. PATENT DOCUMENTS

| | | | |
|---|---|---|---|
| 7,183,066 | B2 | 2/2007 | Fernandez-Salas et al. |
| 7,208,285 | B2 | 4/2007 | Steward et al. |
| 8,137,924 | B2 | 3/2012 | Chapman et al. |
| 9,274,121 | B2 | 3/2016 | Atapattu |
| 2004/0191887 | A1 | 9/2004 | Chapman et al. |
| 2005/0214890 | A1 | 9/2005 | Tan et al. |
| 2006/0134722 | A1 | 6/2006 | Chapman et al. |
| 2009/0191583 | A1 | 7/2009 | Fernandez-Salas et al. |
| 2011/0033866 | A1 | 2/2011 | Fish et al. |
| 2012/0309039 | A1 | 12/2012 | Atapattu |
| 2015/0176051 | A1 | 6/2015 | Fish et al. |
| 2018/0072780 | A1 | 3/2018 | Atapattu |

FOREIGN PATENT DOCUMENTS

| | | | |
|---|---|---|---|
| JP | 2004505636 | A | 2/2004 |
| JP | 2004537313 | A | 12/2004 |
| JP | 2007-520211 | | 7/2007 |
| JP | 2007209227 | A | 8/2007 |
| JP | 2010539477 | A | 12/2010 |
| KR | 20100080530 | A | 7/2010 |
| WO | 2003/012393 | | 2/2003 |
| WO | 2004/031355 | | 4/2004 |
| WO | 2005/076785 | | 8/2005 |
| WO | 2009035476 | A1 | 3/2009 |
| WO | 2012166943 | A1 | 12/2012 |

OTHER PUBLICATIONS

Capek, P. et al., “Sensing the Deadliest Toxin: Technologies for Botulinum Neurotoxin Detection”, Toxins, vol. 2, pp. 24-53, 2010.

Fang, H. et al., “A yeast assay probes the interaction between botulinum neurotoxin serotype B and its SNARE substrate”, Proceedings of the National Academy of Sciences, vol. 103, No. 18, pp. 6958-6963, May 2, 2006.

Hunt, T. et al., “Characterization of SNARE Cleavage Products Generated by Formulated Botulinum Neurotoxin Type-A Drug Products”, Toxins, vol. 2, pp. 2198-2212, 2010.

Ruge, D.R. et al., “Detection of six serotypes of botulinum neurotoxin using fluorogenic reporters”, Analytical Biochemistry, vol. 411, pp. 200-209, 2011.

WIPO, “International Search Report”, International Application No. PCT/US04/42366, Jul. 16, 2006.

WIPO, “International Search Report”, International Application No. PCT/US03/30899, Jun. 9, 2004.

Assay Validation Methods, Adapted from Dr. Robert Mandle, BioSciences Research Associates, Inc., available at https://www.fws.gov/aah/PDF/QI-Terms%20and%20Defs.pdf on Feb. 19, 2020 (4 pages).

Pellett, et al. “Comparison of the primary rat spinal cord cell (RSC) assay and the mouse bioassay for botulinum1 neurotoxin type A potency determination.” journal of Pharmacological and Toxicologist Methods 61 (2010) 304-310. 7 pages.

Clegg, et al. “How Can One Choose the Best Method for Measuring FRET in a Microscope with My Biological System?” Microsc Microanal 11 (Suppl 2), 2005. 2 pages.

(Continued)

*Primary Examiner* — Paul J Holland

(74) *Attorney, Agent, or Firm* — Fish IP Law, LLP

(57) ABSTRACT

Compositions and methods for characterization binding proteins are described that include use of a reporting construct that incorporates a bait region that interacts with the binding protein and a reporter that is susceptible to degradation in the reporter’s local environment. Complex formation between the bait region and the binding protein provides protection of the susceptible reporter from degradation. Such a reporting construct can be utilized to identify cells expressing a binding protein when the susceptible reporter is susceptible to degradation in cytosol.

7 Claims, 7 Drawing Sheets

(56) References Cited

OTHER PUBLICATIONS

Sabine Pellet, "Progress in Cell Based Assays for Botulinum Neurotoxin Detection", Botulinum Neurotxins, Current Topics in Microbiology and Immunology, dated 2013, pp. 257-285.
International Search Report and Written Opinion for International Patent Application No. PCT/US2012/040240, dated Aug. 14, 2012, 9 pages.

COMPOSITIONS AND METHODS FOR CELL-BASED ASSAYS

This application is a continuation of U.S. patent application Ser. No. 15/817,065, filed Nov. 17, 2017, which is a continuation-in-part of U.S. patent application Ser. No. 15/018,621, filed Feb. 8, 2016, which is a continuation of U.S. Pat. No. 9,274,121, filed on May 31, 2012, which claims priority to U.S. Provisional Application No. 61/492,237, filed Jun. 1, 2011. The priority application, along with all other publications referenced herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is protease assays, especially those related to Botulinum toxins.

BACKGROUND

Botulinum neurotoxins (BoNTs) are produced by *Clostridium botulinum*, and are among the most potent toxins known. These toxins are a well-recognized source of food poisoning, often resulting in serious harm or even death of the victims. There are seven structurally related botulinum neurotoxins or serotypes (BoNT/A-G), each of which is composed of a heavy chain (~100 KD) and a light chain (~50 KD). The heavy chain mediates toxin entry into a target cell through receptor-mediated endocytosis. Once internalized, the light chain is translocated from the endosomal vesicle lumen into the cytosol, and acts as a zinc-dependent protease to cleave proteins that mediate vesicle-target membrane fusion ("substrate proteins").

These BoNT substrate proteins include plasma membrane protein syntaxin, peripheral membrane protein SNAP-25, and a vesicle membrane protein synaptobrevin (Syb). These proteins are collectively referred to as the SNARE (soluble N-ethylmaleimide-sensitive factor attachment protein receptor) proteins. Cleavage of SNARE proteins blocks vesicle fusion with plasma membrane and abolishes neurotransmitter release at neuromuscular junction. Among the SNARE proteins, syntaxin and SNAP-25 usually reside on the target membrane and are thus referred to as t-SNAREs, while synaptobrevin is found exclusively with synaptic vesicles within the synapse and is called v-SNARE. Together, these three proteins form a complex that is thought to be the minimal machinery to mediate the fusion between vesicle membrane and plasma membrane. BoNT/A, E, and C[1] cleave SNAP-25, BoNT/B, D, F, G cleave synaptobrevin (Syb), at single but different sites. BoNT/C also cleaves syntaxin in addition to SNAP-25.

Unless the context dictates the contrary, all ranges set forth herein should be interpreted as being inclusive of their endpoints and open-ended ranges should be interpreted to include commercially practical values. Similarly, all lists of values should be considered as inclusive of intermediate values unless the context indicates the contrary.

Due to their threat as a source of food poisoning, and as bioterrorism weapons, there is a need to sensitively and speedily detect BoNTs. In addition, the use of BoNTs for an increasingly wide range of pharmaceutical purposes provides a need to quickly, reproducibly and accurately evaluate the potency and stability of these protein pharmaceutical preparations in order to meet regulatory requirements.

Currently the most sensitive method to detect toxins is to perform in vitro toxicity assay in mice, which is the de facto gold standard. The use of live animals in these studies (which are generally lethality studies), however, raises ethical concerns that have resulted in increasing regulation of this practice. In addition, the imprecision that is inherent in such in vitro studies requires the use of large numbers of mice, is time-consuming, is not readily automated, and cannot be used to study toxin catalytic kinetics.

A number of amplified immunoassay systems based on using antibodies against toxins have also been developed, but most such systems require complicated and expensive amplification process, and cannot be used to study toxin catalytic activity either. Although HPLC and immunoassay can be used to detect cleaved substrate molecules and measure enzymatic activities of these toxins, those methods are generally time-consuming and complicated, some of them require specialized antibodies, making them inapplicable for large-scale screening. In addition, the results of such studies may not correlate well with those of in vitro studies as certain key steps in the toxicity process (for example, cellular internalization and processing) are not represented. Therefore, there is a need for new and improved methods and compositions for detecting BoNTs.

In the last few years, researchers have started investigating use of FRET assays to detect BoNTs. In FRET assays, two fluorogenic amino acid derivatives are used to replace two native amino acids in a short synthetic peptide (12-35 amino acids) that contain toxin cleavage sites. The fluorescence signal of one amino acid derivative is quenched by another amino acid derivative when they are close to each other in the peptide. This mechanism is called "Förster resonance energy transfer" (FRET). Cleavage of the peptide separates the two amino acid derivatives, such that a decrease in FRET can be detected.

FRET assays have been successfully used for detecting BoNTs. (See e.g., US Pat. App. No. 2004/0191887 to Chapman, filed Oct. 28, 2003, US Pat. App. No. 2006/0134722 to Chapman, filed Dec. 20, 2004, U.S. Pat. No. 7,208,285 to Steward (April 2007), U.S. Pat. No. 7,183,066 to Fernandez-Salas (February 2007), and application US2011/0033866 (publ. February 2010), Although some success has been demonstrated in applying FRET assays to detection of BoNTs, the sensitivity and specificity are still undesirable for many purposes.

In FRET assays for the localization of BoNT substrate proteins, for example, measurements relative to the loss of FRET emission upon cleavage of the peptide can suffer from severe interferences, such that in some cases there is no difference between cells treated with no BoNT versus cells treated with saturating concentrations of BoNT. Therefore, it can be said that methods based on the loss of FRET report BoNT induced changes very poorly and thus its low statistical performance and reproducibility render it a non-reliable methodology. The US application 2009/0191583 to Ester Fernandez-Salas claims a non-FRET BoNT assay using only a single fluorophore. The assays disclosed in this document use cells which are capable of efficient Clostridial toxin uptake and which include a membrane localized Clostridial toxin substrate containing a fluorescent marker.

As an example, a cell useful in this paper can express a $SNAP25_{206}$-enhanced green fluorescent protein (EGFP) fusion protein that localizes to the plasma membrane. Upon BoNT/A treatment of this cell, cleavage of the membrane localized $SNAP25_{206}$-EGFP substrate occurs, releasing the EGFP containing fragment into the cytoplasm. Upon excitation of the treated cell with a 484 nM laser, the EGFP is excited and emits light at 510 nM. However, because a portion of the EGFP is now cytoplasmic, a distribution change between the uncleaved, membrane localized $SNAP25_{206}$-EGFP toxin substrate and the cleaved, cytoplasmic localized EGFP fragment can be observed in BoNT/A treated cells. The assay might therefore be adequate for qualitative analysis, but the presence of EGFP emitting portions in both the membrane and the cytoplasm and the absence of a clear and reproducible delineation between these renders this method undesirable for quantitative analysis.

Thus, improved apparatus, systems and methods are therefore still needed which overcome the drawbacks and the limits of the prior art relative to both FRET and non-FRET assays.

SUMMARY OF THE INVENTION

The inventive subject matter relates to a composition for testing presence of an investigative substance, comprising a genetically modified cell having an artificial construct containing a nucleotide sequence that encodes for a hybrid protein having (a) a reporter-containing portion chemically coupled to (b) a cleavage site that interacts with an investigational substance in a manner that cleaves the reporter-containing portion from a remainder of the construct and (c) a control fluorophore selected and positioned in a manner such that, an increased concentration of investigational substance does not lead to a coincidental increase in fluorescent emission of the control fluorophore.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In preferred embodiments, the investigational substance is a Botulinum toxin (BoNT), and the cleavage sequence is appropriately matched with the investigational substance. For example, the BoNT/A, E, and C cleave SNAP-25, and BoNT/B, D, F, G cleave synaptobrevin (Syb), at single but different sites. BoNT/C also cleaves syntaxin in addition to SNAP-25.

Contemplated cleavage site sequences can advantageously comprise (a) a SNARE protein, motif, or mutein. "Muteins" of a protein should be interpreted herein as having at least 30% identity with a corresponding native protein, including for example compositions having at least 35%, 40%, 45%, 50%, 55%, 60%, 65%, 70%, 75%, 80%, 85%, 90%, 95% or 98% identity with the native protein. Variations from identity can comprise any or more of additions, deletions and substitutions. Contemplated muteins include fragments, truncates and fusion proteins.

In other aspects of preferred embodiments, the cleavable reporter-containing portion comprises a fluorescent protein, as for example, Yellow Fluorescent Protein (YFP). YFP is a genetic mutant of green fluorescent protein, derived from *Aequorea Victoria*, and has an excitation peak at 514 nm and emission peak at 527 nm.

Also contemplated for use in the cleavable reporter-containing portion are the closely related Citrine, Venus, and YPet proteins. The modifications have reduced chloride sensitivity, faster maturation, and increased brightness (product of the extinction coefficient and quantum yield). Of course, any of the fluorescent proteins mentioned herein can be modified to include specific characteristics (e.g., spectral) or be truncated to a specific size.

Upon cleavage, the construct is cleaved into two parts, a reporter containing portion that is destroyed or otherwise degraded by the cytosol or other local environment, and a second portion. To normalize the signal detection, that second portion can advantageously include a control fluorophore, preferably at an opposite end from the reporter, which can assist in normalizing the assay. The control fluorophore can, for example, be Cyan Fluorescent Protein (CFP), mCherry, or mStrawberry. As a result of the position of control fluorophore in the construct, an increase in the concentration of BoNT does not lead to a coincidental increase in fluorescent emission of the control fluorophore.

Hybrid protein(s) that are formed in the transfected cells preferably include a transmembrane domain, which tends to locate to intracellular vesicles, and thereby present a vesicle-bound substrate. Heavy chain-mediated endocytosis of the BoNT into the transfected cell is followed by presentation of the light chain on the outer surface of the vesicle, allowing the protease activity of the light chain to cleave the cleavage sequence of the hybrid protein(s), thus cleaving the reporter-containing portion, which then is destroyed or degraded to reduce the signal being tested. Full-length Syb, for example, contains 116 amino acids, and is localized to vesicles through a single transmembrane domain. In some contemplated assays, the membrane-anchoring domain comprises a fragment that contains a palmitoylation site. Suitable membrane-anchoring domains are described, for example, in US 20060134722 to Chapman.

While it is especially preferred that the transmembrane domain is the transmembrane domain of synaptobrevin, mutations (e.g., transitions, transversions, insertions, deletions, inversions, etc.) thereof, and even non-synaptobrevin transmembrane domains are also deemed suitable for use herein. Similarly, it should be appreciated that the transmembrane domain may also be replaced by another polypeptide moiety that allows at least temporary anchoring of the hybrid protein to a membrane such that the remainder of the hybrid protein is exposed to the cytosol.

With respect to the transfected cells expressing the hybrid protein it is generally preferred that the cell is stably transfected. Nevertheless, transient transfection is also contemplated. It is still further typically preferred that the transfected cell is a neuronal cell. However, numerous other non-neuronal cells (including mammalian, rodent, and insect cells and even yeast and bacterial cells) are also contemplated herein. Most typically, the cells will constitutively express the hybrid protein(s) are therefore under appropriate regulatory elements. In alternative aspects, the expression may also be induced.

According to a preferred embodiment, a recombinant nucleic acid molecule, preferably an expression vector, encoding a BoNT substrate polypeptide and a suitable reporter is introduced into a suitable host cell. An ordinarily skilled person can choose a suitable expression vector, preferably a mammalian expression vector, and will recognize that there are enormous numbers of choices. For example, the pcDNA series of vectors, such as pCI and pSi (from Promega, Madison, Wis.), CDM8, pCeo4. Many of these vectors use viral promoters. Preferably, inducible promoters are used, such as the tet-off and tet-on vectors from Clontech (Mountain View, CA).

Many choices of cell lines are suitable as the host cell. Preferably, the cell is of a type in which the respective BoNT exhibits its toxic activities. In other words, the cells preferably display suitable cell surface receptors, or otherwise allow the toxin to be translocated into the cell sufficiently efficiently, and allow the toxin to cleave the suitable substrate polypeptide. Specific examples include primary cultured neurons (cortical neuron, hippocampal neuron, spinal cord motor neuron, etc.); PC12 cells or derived PC12 cell lines; primary cultured chromaffin cells; several cultured neuroblastoma cell lines, such as murine cholinergic Neuro 2a cell line, human adrenergic SK-N-SH cell line, and NS-26 cell line. See e.g. Foster and Stringer (1999), Genetic Regulatory Elements Introduced Into Neural Stem and Progenitor Cell Populations, Brain Pathology 9: 547-567.

The coding region for the reporter/cleavage site construct is under the control of a suitable promoter. Depending on the types of host cells used, many suitable promoters are known and readily available in the art. Such promoters can be inducible or constitutive. A constitutive promoter may be selected to direct the expression of the desired polypeptide. Such an expression construct may provide additional advantages since it circumvents the need to culture the expression hosts on a medium containing an inducing substrate. Examples of suitable promoters would be LTR, SV40 and CMV in mammalian systems; *E. coli* lac or trp in bacterial systems; baculovirus polyhedron promoter (polh) in insect systems and other promoters that are known to control expression in eukaryotic and prokaryotic cells or their viruses. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), .alpha.-amylase (amy), amyloglucosidase (AG—from the glaA gene), acetamidase (amdS) and glyceraldehyde-3-phosphate dehydrogenase (gpd) promoters. Examples of strong yeast promoters are those obtainable from the genes for alcohol dehydrogenase, lactase, 3-phosphoglycerate kinase and triosephosphate isomerase. Examples of strong bacterial promoters include $SPO_2$ promoters as well as promoters from extracellular protease genes.

Hybrid promoters may also be used to improve inducible regulation of the expression construct. The promoter can additionally include features to ensure or to increase expression in a suitable host. For example, the features can be conserved regions such as a Pribnow Box or a TATA box. The promoter may even contain other sequences to affect (such as to maintain, enhance or decrease) the levels of expression of the nucleotide sequence. For example, suitable other sequences include the Shl-intron or an ADH intron. Other sequences include inducible elements, such as temperature, chemical, light or stress inducible elements. Also, suitable elements to enhance transcription or translation may be present. An example of the latter element is the TMV 5' signal sequence (see Sleat, 1987, Gene 217: 217-225; and Dawson, 1993, Plant Mol. Biol. 23: 97).

The expression vector may also contain sequences which act on the promoter to amplify expression. For example, the SV40, CMV, and polyoma cis-acting elements (enhancer) and a selectable marker can provide a phenotypic trait for selection (e.g. dihydrofolate reductase or neomycin resistance for mammalian cells or ampicillin/tetracycline resistance for *E. coli*). Selection of the appropriate vector containing the appropriate promoter and selection marker is well within the level of those skilled in the art.

Preferably, the coding region for the construct is under the control of an inducible promoter. In comparison to a constitutive promoter, an inducible promoter is preferable because it allows for suitable control of the concentration of the reporter in the cell, therefore the measurement of changes in signals are greatly facilitated.

For example, expression can be controlled using the Tet-on & Tet-off system Clontech (Mountain View, CA). Under the control of this promoter, gene expression can be regulated in a precise, reversible and quantitative manner. Briefly, for Tet-on system, the transcription of downstream gene only happens when doxycycline is present in the culture medium. After the transcription for a certain period of time, one can change culture medium to deplete doxycycline, thus, stop the synthesis of new reporter proteins. Therefore, there is no background from newly synthesized reporter proteins, and one may be able to see a faster change after toxin treatment.

Local environments for the construct other than living cells are also contemplated, including for example, cytosol of lysed cells, and synthetic media that contains one or more enzymes capable of degrading the cleavable fragment when cleaved from the reporter molecule, but incapable or much less capable of degrading the cleavable fragment prior to cleavage from reporter molecule.

It is further contemplated to provide an isolated polynucleotide molecule encoding a construct described above. The construct is preferably an expression vector comprising the polynucleotide molecule operably linked to a promoter. A preferable promoter is an inducible promoter.

BRIEF DESCRIPTION OF THE DRAWINGS

FIG. 1A depicts a construct of the inventive concept. FIG. 1B depicts a method of the inventive concept, where the construct is cleaved by a botulinum toxin.

FIG. 2A shows photomicrographs of transformed cells and transformed cells following exposure to BoNT/A. FIG. 2B graphically depicts results of fluorescence emissions measurements from transformed cells exposed to BoNT/A and control transformed cells. FIG. 2C shows results of SDS-PAGE followed by immunoblotting and probing with anti-SNAP-25 of the products of exposure of various constructs to BoNT/A.

DETAILED DESCRIPTION

Various objects, features, aspects and advantages of the inventive subject matter will become more apparent from the following detailed description of preferred embodiments, along with the accompanying drawing figures in which like numerals represent like components.

Figure 1A:
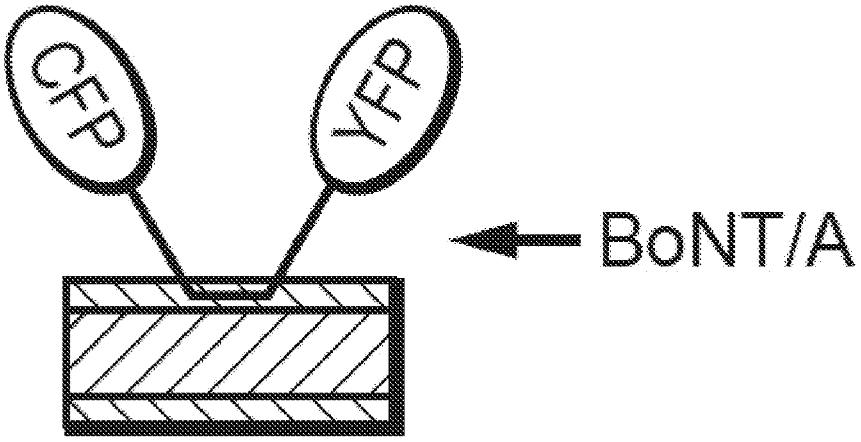
FIGS. 1A and 1B schematically depict an exemplary construct and method of the inventive concept.
Figure 1B:
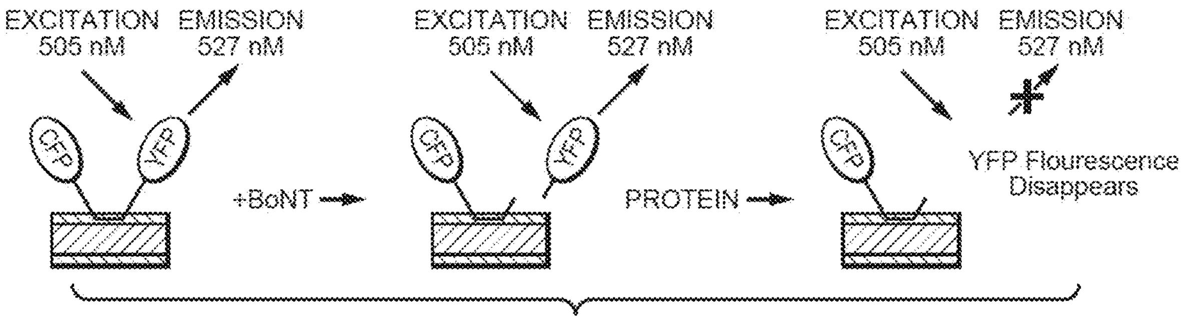

FIGS. 1A and 1B diagram a construct and an exemplary assay in which BoNT/A cell-based reporters are used to detect BoNT/A activity by loss of YFP fluorescence.

FIG. 1A schematically depicts BioSentinel's BoCell™ A BoNT/A construct. The reporter fluorophore, YFP, and the normalization fluorophore, CFP, are coupled by a cleavage sequence, SNAP-25 (green). SNAP-25 palmitoylation localizes the reporter to a plasma membrane.

FIG. 1B shows detection of BoNT/A activity by loss of YFP fluorescence. The YFP moiety is directly excited leading to fluorescence emission in the absence of BoNT/A. Cleavage of the reporter by BoNT/A releases a C-terminal reporter fragment containing the YFP moiety into the cytosol. The fragment is rapidly degraded and, thus, YFP emission is lost. The CFP signal is still used to control for cell-to-cell reporter expression levels and cell density.

Figure 2A:
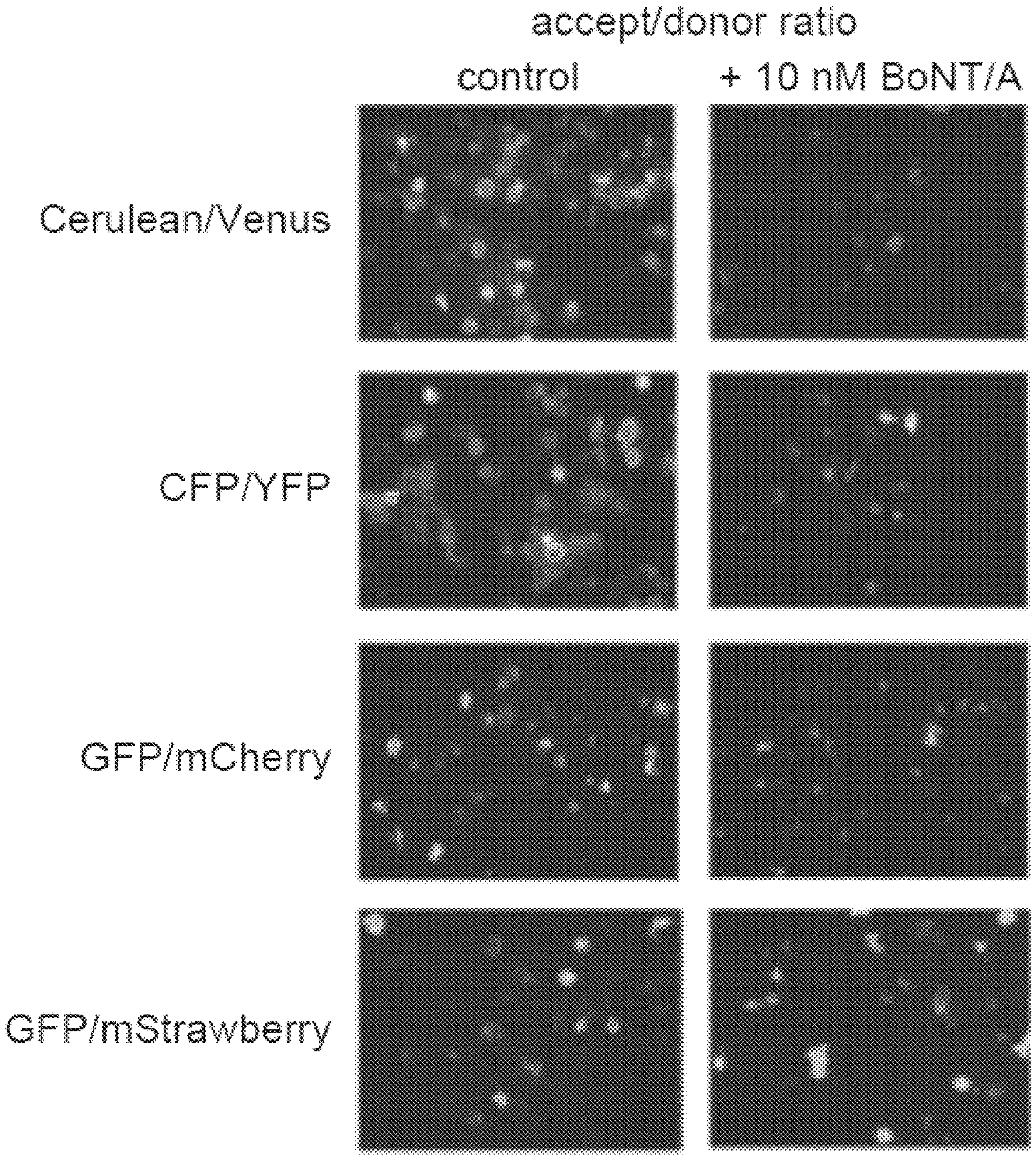
FIGS. 2A, 2B, and 2C depict results obtained from testing of different reporting constructs.
Figure 2B:
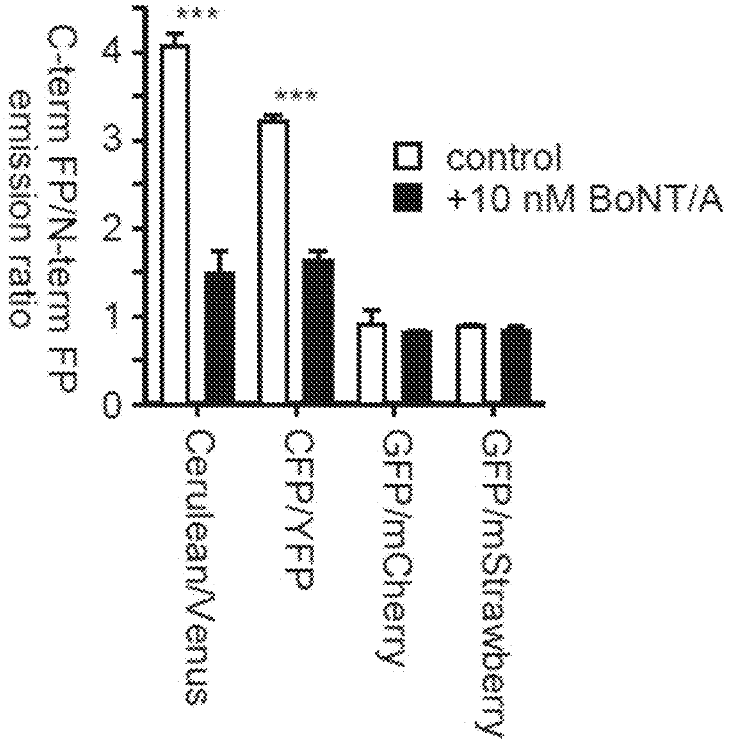
Figure 2C:
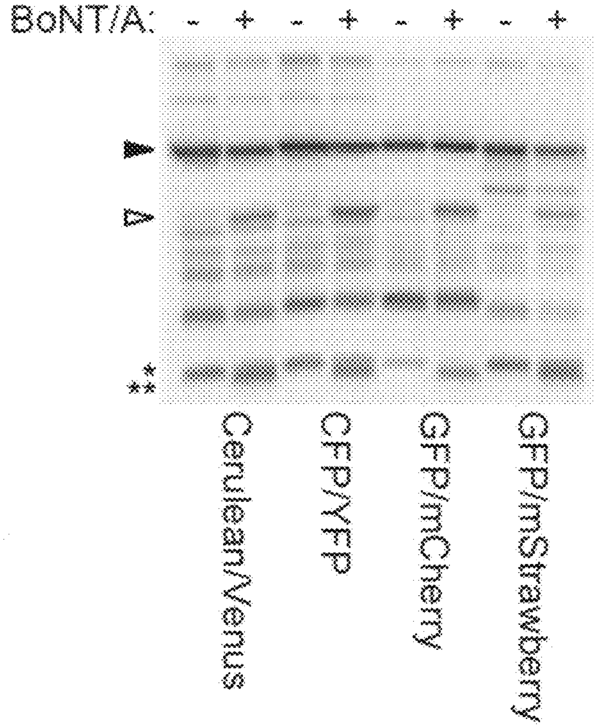

Surprisingly, not all fluorescent proteins related to YFP are effective as the reporter fluorophore. For example, FIGS. 2A, 2B, and 2C provide evidence that reporters containing YFP or the closely related derivative Venus can detect BoNT/A activity in cells, but not mCherry or mStrawberry. Here, Neuro2A cells were grown in a 96-well plate to 70% confluency and transiently transfected using Lipofectamine 2000 (Invitrogen™), with reporters containing the indicated N-terminal and C-terminal (N-term/C-term) fluorophore pairs. After 24 h, cells were incubated in the presence or absence of 10 nM BoNT/A at 37° C. for 72 h in 100 μl of phenol red-free MEM medium.

FIG. 2A shows BoNT/A-induced changes in fluorescence responses. Semi-automated YFP and CFP fluorescence measurements were performed using a Nikon™ TE2000-U fluorescent microscope with 20× magnification and Nikon NIS Elements 3.4 software. Shown are randomly selected fields pseudo-colored for the C-terminal/N-terminal fluorescent protein (FP) fluorescence ratio. Ratios were calculated from emissions collected upon direct excitement of each fluorophore.

FIG. 2B represents fluorescence ratios and BoNT/A sensitivities of the cell-based reporters. 30 randomly selected cells per condition were analyzed for fluorescence ratios in the presence or absence of 10 nM BoNT/A. The average signal from the 30 cells from 5 microscopic fields on 3 different wells is shown. Cells exhibiting over-saturated fluorescence were excluded.

FIG. 2C shows a blot showing that BoNT/A was active in cells regardless of the reporter. All reporters show some cleavage in the presence of BoNT/A, and all native SNAP25s are cleaved. Cells were transfected and treated with BoNT/A as described above but scaled up into 6-well plates. After 72 h incubation with BoNT/A, cells were washed 3× with serum-free MEM, collected by scraping, and lysed using M-Per Lysis Buffer (Pierce™). 40 μg of cell lysate was subjected to SDS-PAGE before transfer to nitrocellulose paper and immunoblot analysis using an antibody directed against SNAP-25 (clone 71.2, Synaptic Systems). Arrows indicate the position of the full-length (closed) and cleaved (open) forms of the reporters. Full-length (*) and cleaved (**) native SNAP-25 are indicated.

Viewed from another perspective, the inventive subject matter can be extended beyond cleavable substrates, to any assay having a construct with a reporter that can be deprotected, and then degraded in some manner by the cytosol or other local environment. For example, a susceptible reporter could be modified to include a 'bait' domain that is used to screen against a library of recombinant proteins that could possibly bind with the bait domain. Without the bait domain protected by a binding protein, the susceptible reporter will be degraded. In such an assay, cells expressing binding proteins will form a complex to protect the susceptible reporter from degradation, while cells expressing a binding partner to the bait will light up. The bait domain could advantageously be a small peptide, and the binding partners could be members of a library of proteins (or protein mutants). The system could also be reversed such that there is a library of bait domains tested against a single test protein (or test protein library).

In each of these instances it is considered advantageous to include a second reporter that is not degraded post-exposure by the cytosol or other local environment, or is at least degraded much more slowly post-exposure than the first reporter.

Still further, whereas the reporter can conveniently be selected from suitable fluorophores, it is contemplated that the reporter could be replaced or augmented by any other protein or other component with a defined function that is known to (a) have a relatively fast turnover in the cell without protection, and (b) that can be protected by interaction with a binding partner. Defined functions include transcription activators for reporter gene, repressors for lethal genes, etc. (anything that can be easily identified or selected against).

Figure 3:
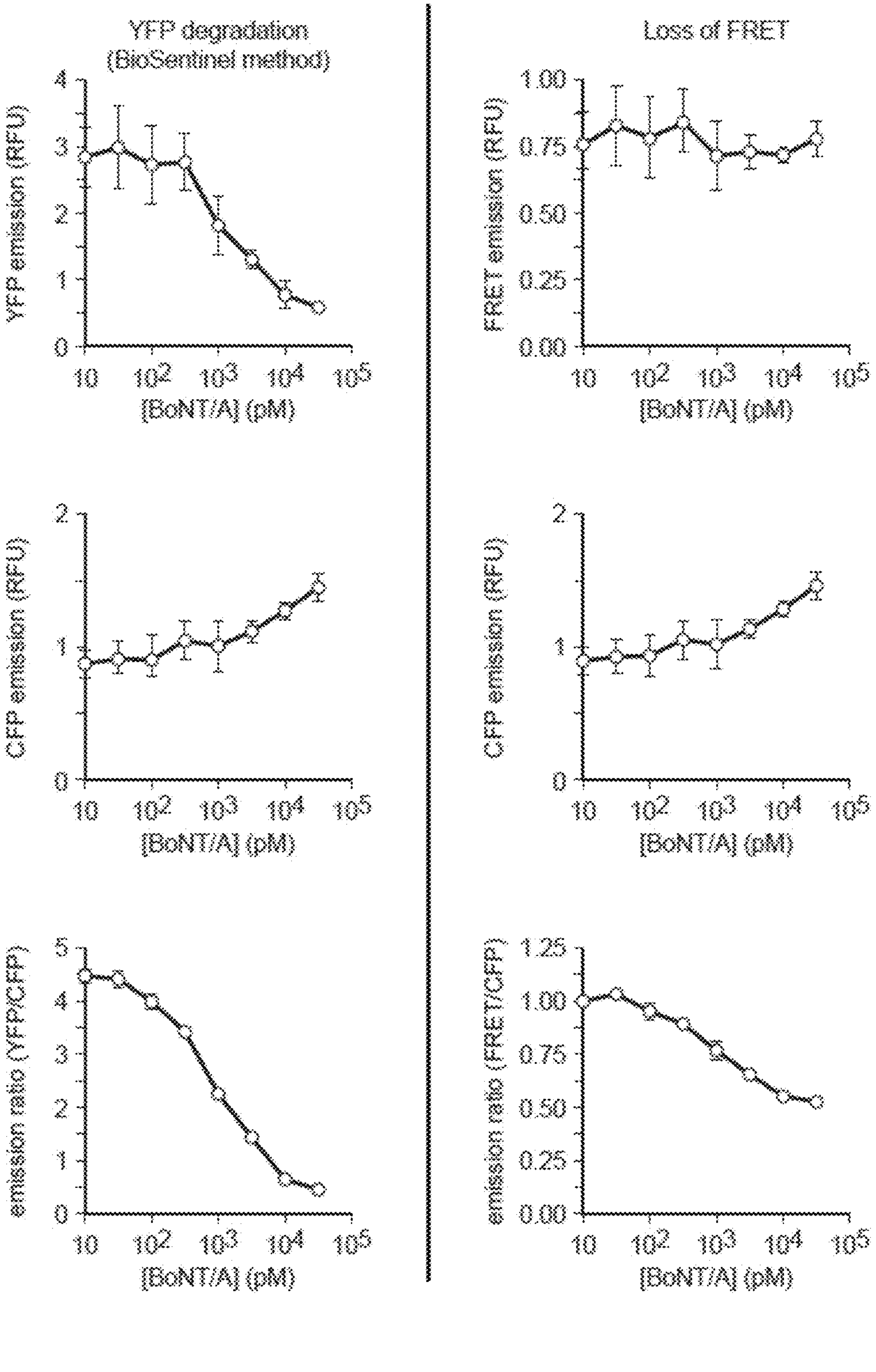
FIG. 3 graphically depicts the results of fluorescence measurements from transformed cells expressing a reporting construct of the inventive concept. Results from the same set of cells are shown for the BioSentinel method (based upon characterization of YFP degradation) on the left, and for the prior art method based on FRET emission (Loss of FRET) from the construct on the right.

FIG. 3 shows an embodiment in which data was collected for both YFP degradation and loss of FRET according to the state of the art practice from the exact same plates of cells. For YFP degradation, directly and singularly excited YFP emissions (top, Ex500, Em526) and CFP emissions (middle, Ex434, Em470) are collected. Those emission are then background subtracted and the YFP emission is divided by CFP emission to control for cell density and reporter expression in the individual wells. That emission ratio (YFP/CFP, bottom) is then used for the essay report.

For loss of FRET, FRET emissions (top, Ex434, Em526) and CFP emissions (middle, Ex434, Em470) are collected. Those emissions are then background subtracted, and the FRET emission is divided by CFP emission to control for cell density and reporter expression in the individual wells. That emission ratio (FRET/CFP, bottom) is shown here to compare to the normal method.

The key comparison is the loss of directly excited YFP versus the loss of FRET emission. From the comparison between the measurements and the corresponding curves, it becomes immediately apparent that the overall dynamic range for YFP degradation is much larger than the dynamic range of loss of FRET emissions. In some cases, there is no difference, statistically, between cells treated with no BoNT versus sells treated with saturating concentrations of BoNT when looking solely at the raw FRET emissions. For the loss of FRET method, the BoNT dose response only becomes clear after dividing the FRET emission by the CFP (donor) emission. The CFP (donor) emission shows a small increase emission due to de-quenching in response to reporter cleavage.

In summary, the loss of FRET method reports BoNT-induced changes in the reporter very poorly, or not at all, and therefore cannot be therefore used for a correct qualitative and quantitative determination. In contrast, preferred methods contemplated herein have a high degree of specificity and reproducibility, which allow one to rely on the data for both the qualitative and quantitative analysis.

Genetic Construction of Alternative Reporters

Twenty alternate fluorophore constructs were generated in four plasmid backgrounds. Below is the internal name of each construct with a brief description of the background and cloned fragment. A more detailed summary of the construction methods follows.

| Construct Name | Plasmid Background | Description | Alternative Reporter Mechanism |
|---|---|---|---|
| pMD0076a | pcDNA4/TO | mRaspberry-SNAP-YFP | 1 |
| pMD0076b | pcDNA4/TO | mCherry-SNAP-YFP | 1 |
| pMD0077 | pIRES | SNAP-YFP, CFP | 3 |
| pMD0078 | pECFP-C1 (Modified) | Synapsin promoter, SNAP-YFP | 2 |
| pMD0079 | pcDNA4/TO | SNAP-YFP | 2 |
| pMD0080 | pECFP-C1 (Modified) | SNAP-YFP | 2 |
| pMD0081 | pECFP-C1 (Modified) | mRaspberry-SNAP-YFP | 1 |
| pMD0082 | pECFP-C1 (Modified) | mCherry-SNAP-YFP | 1 |
| pMD0090 | pIRES | SNAP-Venus, CFP | 3 |
| pMD0091 | pcDNA4/TO | SNAP-Venus | 2 |
| pMD0092 | pECFP-C1 (Modified) | SNAP-Venus | 2 |
| pMD0097 | pcDNA4/TO | mKate2-SNAP-YFP | 1 |
| pMD0098 | pcDNA4/TO | TagRFP-SNAP-YFP | 1 |
| pMD0099 | pECFP-C1 (Modified) | mKate2-SNAP-YFP | 1 |
| pMD0100 | pECFP-C1 (Modified) | TagRFP-SNAP-YFP | 1 |
| pMD0103 | pBudCE4.1 | SNAP-YFP, CFP | 3 |
| pMD0104 | pBudCE4.1 | SNAP-YFP, mRaspberry | 3 |
| pMD0105 | pBudCE4.1 | SNAP-YFP, mCherry | 3 |
| pMD0106 | pBudCE4.1 | SNAP-Venus, CFP | 3 |
| pMD0107 | pBudCE4.1 | SNAP-Venus, mRaspberry | 3 |
| pMD0108 | pBudCE4.1 | SNAP-Venus, mCherry | 3 |

pMD0076a, pMD0076b, pMD0097, and pMD0098

Constructs were generated by amplifying the mRaspberry, mCherry, mKate2, and TagRFP fluorophores with engineered KpnI and XhoI restriction sites. The amplified fragments and the previously used pcDNA4/TO BoCell vector generated were then digested with KpnI/XhoI. The vector DNA, minus the excised CFP, was then ligated with the mRaspberry, mCherry, mKate2, and TagRFP fragments to create the final vectors.

pMD0079 and pMD0091

For pMD0079, SNAP YFP was amplified with engineered BamHI and XhoI restriction sites. The amplified fragment and pcDNA4/TO vector DNA were then digested with BamHI/XhoI and then ligated together. pMD0091 was then generated by amplifying the Venus fluorophore with engineered EcoRI and XbaI restriction sites. The amplified Venus fragment and pMD0079 were then digested with EcoRI/XbaI. The pMD0079 vector DNA, minus the excised YFP, was then ligated with the Venus fragment to create pMD0091.

pMD0077 and pMD0090

For pMD0077, SNAP YFP was amplified with engineered NheI and XhoI restriction sites. The amplified fragment and pIRES vector DNA were then digested with NheI/XhoI and then ligated together. The CFP fluorophore was then amplified with engineered XbaI/NotI restriction sites. The amplified fragment and previously generated SNAP YFP-containing pIRES vector were then digested with XbaI/NotI and ligated together to create pMD0077. pMD0090 was then generated by amplifying the Venus fluorophore with engineered EcoRI and MluI restriction sites. The amplified Venus fragment and pMD0077 were then digested with EcoRI/MluI. The pMD0077 vector DNA, minus the excised YFP, was then ligated with the Venus fragment to create pMD0090.

pMD0078 and pMD0080

For pMD0080, SNAP YFP was amplified with engineered NheI and XhoI restriction sites. Then amplified fragment and pECFP-C1 were then digested with NheI/XhoI. The vector DNA, minus the excised CFP, was then ligated with the SNAP YFP to create pMD0080. pMD0078 was then generated by amplifying the synapsin promoter with engineered AseI and NheI restriction sites. The amplified fragment and pMD0080 were then digested with AseI/NheI. The pMD0080 vector DNA, minus the excised CMV promoter, was then ligated with the synapsin promoter to create pMD0078.

pMD0081, pMD0082, pMD0099, pMD0100

Constructs were generated by amplifying the mRaspberry, mCherry, mKate2, and TagRFP fluorophores with engineered NheI and XhoI restriction sites. The amplified fragments and original BoCell construct from Min (pECFP-C1 background) were then digested with NheI/XhoI. The BoCell construct, minus the excised CFP fragment, was then ligated with the mRaspberry, mCherry, mKate2, and TagRFP fragments to create pMD0081, pMD0082, pMD0099, and pMD0100.

pMD0092

For pMD0092, the Venus fluorophore was amplified with engineered EcoRI and XbaI restriction sites. The amplified fragment and pMD0080 were then digested with EcoRI/XbaI. The pMD0080, minus the excised YFP fragment, was then ligated with the Venus fragment to generate pMD0092.

pMD0103, pMD0104, and pMD0105

The SNAP YFP construct was amplified with engineered XbaI and BamHI restriction sites. The amplified fragment and pBudCE4.1 vector were then digested with XbaI/BamHI and ligated together. The CFP, mRaspberry, and mCherry fluorophores were then amplified with engineered KpnI and BglII restriction sites. The amplified fragments and previously generated pBudCE4.1 vector containing SNAP YFP were then digested with KpnI/BglII and ligated together to generate pMD0103, pMD0104, and pMD0105.

pMD0106, pMD0107, and pMD0108

The SNAP Venus construct was amplified with engineered XbaI and BamHI restriction sites. The amplified fragment and pBudCE4.1 vector were then digested with XbaI/BamHI and ligated together. The CFP, mRaspberry, and mCherry fluorophores were then amplified with engineered KpnI and BglII restriction sites. The amplified fragments and previously generated pBudCE4.1 vector containing SNAP Venus were then digested with KpnI/BglII and ligated together to generate pMD0106, pMD0107, and pMD0108.

Primary Screening of the Alternative Reporters

Neuro2A cells were seeded into 96-well plates and allowed to expand 24-48 h before transiently transfecting the cells using the above genetic constructs and Lipofectamine 2000™ according to the manufacturer's instructions. Transfected cells were allowed to recover for 24 hr before applying 0 or 30 nM BoNT/A holotoxin and incubating the cells an additional 24 hr at 37° C., 5% $CO_2$. Cells were then imaged using a Nikon-TE2000U fluorescence microscope taking a minimum of three images per condition. Fluorescence emissions were collected using filters appropriate for the listed fluorophores. Total fluorescence emissions were also collected using a Varioskan™ fluorescence microplate reader using appropriate excitation and emission wavelength settings.

Fluorescence microscopy data was processed to gate out over expressing (saturated) cells based on pixel intensities for a given channel. Total emissions from each channel were then collected and, when indicated, the BoNT/A-responsive YFP or Venus emissions were divided by the BoNT/A-unresponsive CFP, RFP (mKate2, mRaspberry, or mCherry), or exogenously added membrane dye (Alternative Reporter 2) emissions.

Each reporter construct, using the data collected above, was analyzed for the following: Cellular targeting of each reporter was judged by the presence of uniform fluorescence expression on the plasma membrane. Poor plasma membrane targeting was associated with the presence of bright, punctate spots within the cell. Reporters lacking plasma membrane targeting were eliminated from further consideration. Total fluorescence emissions and, thus total reporter expression, were judged by the emissions of a given fluorescent probe relative to background emissions. Probes that did not give a signal >2 times that of background were eliminated from further consideration.

Secondary Screening of the Alternative Reporters: BoNT/A-Dose Responses

Genetic constructs that passed primary screening were transiently transfected into cells as described above but using varying DNA concentrations. Varying the DNA concentration generated cells with varying levels of reporter expression. After transfection and a 24 hr recovery period, the transfected cells were titrated with 10 pM to 30 nM BoNT/A allowed to further incubate. After incubation, fluorescence emissions were collected using a Varioskan fluorescence microplate reader using appropriate excitation and emission wavelength settings. For all experiments, test reporter responses were directly compared to the current BoCell reporter CFP-SNAP25-YFP that was transiently transfected in parallel.

Fluorescence emissions for the BoNT/A-response YFP were divided by the BoNT/A-unresponsive CFP, RFP (mKate2, mRaspberry, or mCherry), or exogenously added membrane dye (Alternative Reporter 2) emissions generating an emission ratio. The emission ratio was then plotted as a function of BoNT/A concentration. Data was compared to the BoCell reporter. Test reporter suitability was qualitatively assessed by comparison to the BoCell reporter: Does BoNT/A elicit a similar response with the test reporter compared to the current BoCell reporter?

Secondary Screening of the Alternative Reporters: FRET Emissions

Reporter genetic constructs were transfected into cells plated on glass cover slips using Lipofectamine according to the manufacturer's protocol. For each construct, single fluorophore controls were also transfected. After a 24 hr recovery period, cells were treated with or without 30 nM BoNT. Using the controls for each reporter, images were captured by fluorescence microscopy and the images used to calibrate FRET determinations by a three-filter set method. Reporters were then evaluated for FRET efficiency in the presence and absence of BoNT/A. For all experiments, test reporter responses were directly compared to the current BoCell reporter CFP-SNAP25-YFP that was transiently transfected in parallel. Each test reporter was evaluated for the presence of FRET and whether FRET emissions were responsive to BoNT/A. The conclusion was that FRET emissions do not represent a reliable screening method, in line with the conditions already observed in example 3.

Stability Testing and Performance Relative to In Vivo Mouse Time-of-Death Assay

As noted above, conventional in vitro mouse time-of-death assays for BoNT potency (as are typically used for stability studies in pharmaceutical preparations) have numerous disadvantages, including expense and increasing objections to such testing on ethical grounds. Surprisingly, Inventors have found that composition and methods of the inventive concept provide results that are essentially statistically equivalent (i.e. having a $r^2$ value that exceeds 0.95) to those provided by in vivo studies approved for pharmaceutical industry use in BoNT characterization. In addition, Inventors have found that the reproducibility of cell-based assays of the inventive concept that are directed to BoNT toxin potency demonstrate greatly improved reproducibility relative to such in vivo mouse time-of-death assays. The CV of repeated measurements from a sample made using a cell-based assay of the inventive concept can be less than 50%, less than 40%, less than 30%, less than 25%, less than 20%, less than 15%, and/or less than 10% of a conventional in vivo mouse time-of-death assay that is approved for pharmaceutical use and performed on the same sample.

Figure 4:
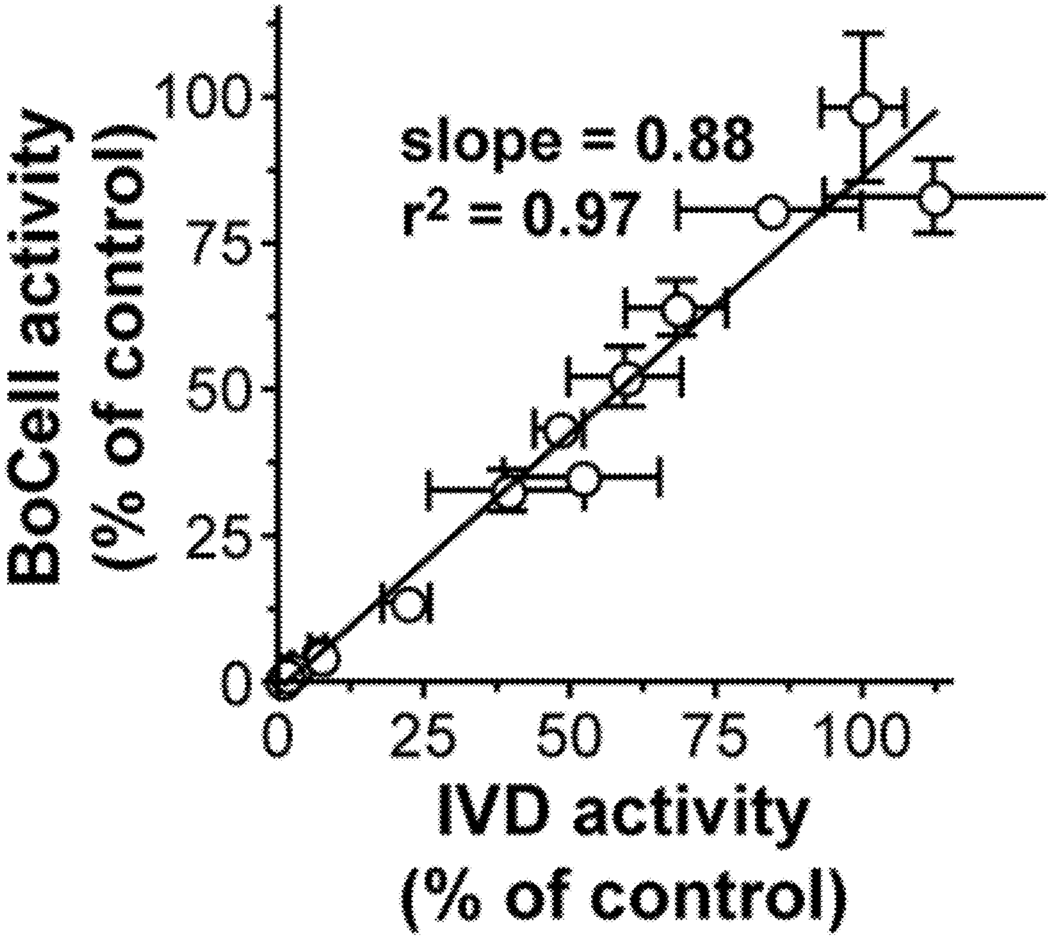
FIG. 4 shows a graphical depiction of data comparing the performance of a cell-based assay of the inventive concept to a prior art, regulatory agency approved in vitro mouse time-of-death assay for BoNT/A potency following incubation at elevated temperatures for different periods of time.

An example of this is shown in FIG. 4. FIG. 4 shows the results of characterization of the potency of BoNT/A neurotoxin incubated at elevated temperature (40° C.) for different periods of time. The same samples were characterized using an in vitro cell-based assay of the inventive concept and by an in vivo mouse time-of-death study performed by a pharmaceutical company using established and regulatory agency-approved testing protocols. Results are shown as a percentage of the value determined for a control sample that was not exposed to elevated temperatures. The coefficients of variation are shown as error bars. In this example the correlation coefficient indicate an extremely high degree of correlation between the results of the two methods ($r^2$=0.97). In addition it is evident that the cell-based method is more reproducible than an approved in vitro assay, with CVs that are typically less than 25% of that of an in vitro assay performed on the same sample.

Such potency assays are particularly useful for characterizing stability. In such stability studies samples of a pharmaceutical preparation (for example, a preparation that includes BoNT/A) are stored at a temperature that is elevated relative to the conventional storage temperature. For example, for a preparation normally stored at 2° C. to 8° C. such stability testing can be performed by exposing samples of a pharmaceutical preparation to temperatures of 15° C., 20° C., 25° C., 30° C., 35° C., 37° C., 40° C., 45° C., 50° C. or higher for various periods of time. Following such treatment the activity or potency of the heated samples can be characterized and compared to that of the pharmaceutical preparation that has not been subjected to heat treatment. The loss of potency over time can be used to estimate a shelf life for the pharmaceutical preparation when stored at recommended temperatures, for example by comparison to a correlation between accelerated and real-time aging at the recommended temperature or through application of the Arrhenius equation. It should be appreciated that the higher degree of precision provided by cell-based assays of the inventive concept improve the accuracy of such estimations, with the high degree of correlation to the in vivo mouse lethality assay providing assurance that the observed loss of potency would also be observed in actual use.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms “comprises” and “comprising” should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of identifying a reporting construct suitable for use in a cell-based assay for characterization of a botulinum neurotoxin, comprising:

transforming a cell susceptible to intoxication with the botulinum neurotoxin with an expression vector encoding a hybrid protein comprising (a) a membrane binding domain, (b) a reporter-containing domain comprising a degradable reporter that is degraded in the cell's cytosol within a time course of the cell-based assay, (c) a linking region comprising a soluble N-ethylmaleimide-sensitive fusion protein attachment protein receptor (SNARE) or fragment thereof comprising a cleavage site that interacts with the botulinum toxin in a manner that cleaves the reporter-containing domain from remainder of the hybrid protein and is interposed between the membrane binding domain and the reporter-containing domain, and (d) a control domain comprising a control reporter domain coupled to the membrane binding domain;

characterizing targeting of a plasma membrane of the cell by the reporting construct by obtaining an image of the cell by fluorescence microscopy;

characterizing background fluorescence intensity and fluorescence intensity of the cell;

contacting a plurality of the cells with the botulinum neurotoxin at a plurality of concentrations, wherein each of the plurality of concentrations us from 10 pM to 30 nM;

after contacting the plurality of the cells with the botulinum neurotoxin, obtaining a first fluorescence measurement at a first wavelength corresponding to an emission wavelength of the degradable reporter and a second fluorescence measurement at a second wavelength corresponding to an emission wavelength of the control reporter; and plotting an emission ratio comprising the first fluorescence measurement divided by the second fluorescence measurement against concentration of the botulinum neurotoxin, wherein plasma membrane targeting comprises uniform fluorescence over the plasma membrane and wherein fluorescence intensity of the cell is at least twice background intensity.

2. The method of claim 1, wherein the degradable reporter is a first fluorescent peptide.

3. The method of claim 2, wherein the first fluorescent peptide is selected from the group consisting of Yellow Fluorescent Protein (YFP), Citrine, Venus, and a YPet protein.

4. The method of claim 1, wherein the control reporter comprises a second fluorophore.

5. The method of claim 4, wherein the control reporter is a second fluorescent peptide.

6. The method of claim 5, wherein the second fluorescent peptide is selected from the group consisting of CFP, mStrawberry, and mCherry.

7. The method of claim 1, wherein the SNARE is selected from the group consisting of SNAP-25, synaptobrevin, and syntaxin.

* * * * *